United States Patent
Tseng et al.

(10) Patent No.: US 7,912,547 B2
(45) Date of Patent: Mar. 22, 2011

(54) DEVICE FOR OPTIMIZING TRANSMITTING ENERGY AND TRANSMITTING POSITION FOR AN IMPLANTABLE ELECTRICAL STIMULATOR

(75) Inventors: Kuo Hua Tseng, Hsinchu County (TW); Yu Kon Chou, Hsinchu County (TW); Pei Ying Shieh, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 215 days.

(21) Appl. No.: 11/907,148

(22) Filed: Oct. 10, 2007

(65) Prior Publication Data

US 2008/0039899 A1    Feb. 14, 2008

Related U.S. Application Data

(62) Division of application No. 11/210,819, filed on Aug. 25, 2005, now abandoned.

(30) Foreign Application Priority Data

May 3, 2005 (TW) ................................ 94114273 A

(51) Int. Cl.
*A61N 1/02* (2006.01)

(52) U.S. Cl. .......................................... 607/32; 607/33
(58) Field of Classification Search ............. 607/32–33, 607/60–61
See application file for complete search history.

(56) References Cited

U.S. PATENT DOCUMENTS

| | | | | |
|---|---|---|---|---|
| 5,876,425 | A * | 3/1999 | Gord et al. | 607/56 |
| 6,553,263 | B1 * | 4/2003 | Meadows et al. | 607/61 |
| 6,810,289 | B1 * | 10/2004 | Shaquer | 607/57 |
| 7,512,443 | B2 * | 3/2009 | Phillips et al. | 607/61 |

* cited by examiner

*Primary Examiner* — Scott M Getzow
*Assistant Examiner* — Amanda Patton
(74) *Attorney, Agent, or Firm* — Bacon & Thomas, PLLC

(57) ABSTRACT

A device for optimizing transmitting energy and transmitting position for an implantable electrical stimulator is provided. The device utilizes a design of a wireless energy transmitting and positioning device with an external energy-feedback control, which can automatically detect an optimum energy-transmitting position through an external antenna performing an adjustable energy transmission method, and through a wireless-feedback control method to provide the optimum energy. As such, the implantable electrical stimulator can exactly and effectively stimulate the nervous muscle.

7 Claims, 3 Drawing Sheets

DEVICE FOR OPTIMIZING TRANSMITTING ENERGY AND TRANSMITTING POSITION FOR AN IMPLANTABLE ELECTRICAL STIMULATOR

This application is a divisional of U.S. patent application Ser. No. 11/210,819 filed Aug. 25, 2005, which is incorporated by reference herein.

BACKGROUND OF THE INVENTION

1. Field of the Invention

The present invention relates to a device for transmitting energy and transmitting position for an implantable electrical stimulator, and more particularly to a device for transmitting energy and transmitting position, the device uses a wireless energy-feedback control to determine the optimum transmission energy and the optimum energy-transmitting position of the implantable electrical stimulator.

2. Description of the Related Art

Electrical stimulator combines the principles of Chinese traditional Point Percussion Therapy and western TENS (Transcutaneous Electrical Nerve Stimulation). The stimulator uses micro electric current to stimulate specific acupuncture points to achieve the health care effect. That is it can stimulate the self-cure mechanism of the body with an electric current having suitable intensity and frequency continuously, gently stimulating the nerve, the muscle and the cell. On clinical uses, the method of treatment is divided into the Transcutaneous Electrical Nerve Stimulation (TENS) and the Electrical Muscle Stimulation(EMS).

The electrical stimulation has been widely utilized for the function of recovery. Recently, as a result of the breakthrough of the micro electron technology, the micro mechanical and electrical technology, the biological material and the biological compatible seal technology, the electrical stimulator tends to have a small and implantable form.

FIG. 1 is a conventional implantable electrical stimulator comprising an in vivo electrical stimulating module 10 and an in vitro energy-transmitting module 12. The in vivo electrical stimulating module 10 includes a circuit board 100; an in vivo energy-transmitting coil 102 and a pair of positive/negative electrode 104 provided on the circuit board 100; and a biological compatible polymer layer 106 covering the whole in vivo electrical stimulating module 10. The in vitro energy-transmitting module 12 includes an in vitro control module 120 and an in vitro energy-transmitting coil 122. The in vitro control module 120 will drive the in vitro energy-transmitting coil 122 to emit wireless energy. The wireless energy will be received by the in vivo energy-transmitting coil 102 and converted by the circuit board 100 into a voltage source. The converted voltage source will be applied on the positive/negative electrode 104 to generate an electrical stimulating current.

As mentioned above, the conventional implantable electrical stimulator transmits the energy from an external antenna module to an in vivo implantable electrical stimulating element via radio frequency (RF) and receive the energy by an internal electronic component to automatically generate an electrical stimulation, rather than stimulating the nervous muscle with an electrical line penetrating through the skin, thus can reduce the probability of wound infection. At present, however, the energy needed by conventional implantable electrical stimulating devices is unidirectionally transmitted into these conventional implantable electrical stimulating devices via an antenna. That is, the energy is transmitted to the in vivo electrical stimulating module via an external energy-transmitting antenna to stimulate the nervous muscle. In operation, this energy-transmitting method may suffer from the displacement of the implanted electrical stimulating element or the electromagnetic interference from surrounding environment and thus change the properties of the energy-transmitting circuit, thereby causing to transmit excessive energy to result in heat-generating from the implantable electrical stimulating element, or causing to transmit too few energy to result in abnormal operation or even malfunction, thereby further causing unnecessary damage to the human body. In addition, effective detection of the position of the implantable electrical stimulating element and provision of effective energy-transmission are also general issues encountered by domestic and foreign implantable electrical stimulators.

In brief, the energy-transmitting process of conventional implantable electrical stimulators has the following disadvantages:

1. The correct position of the implantable electrical stimulator is not easy to detect.
2. Control of the power-transmitting does not come easy.
3. Properties of the energy-transmitting circuit easily suffer from electromagnetic interference from surrounding environment.

Accordingly, there is a need for providing a device for optimizing transmitting energy and transmitting position for an implantable electrical stimulator in order to solve those problems mentioned above.

SUMMARY OF THE INVENTION

The primary object of the present invention is to provide a device for optimizing transmitting energy and transmitting position for an implantable electrical stimulator, which uses a wireless-feedback control method to provide the optimum wirelessly transmitting energy and detect the position for optimizing transmitting energy, such that the implantable electrical stimulator can exactly and effectively stimulate the nervous muscle.

Another object of the present invention is to provide a device for optimizing transmitting energy and transmitting position for an implantable electricai stimulator, which utilizes a design of optimizing transmitting energy and transmitting position such that the implantable electrical stimulator can be used more comfortable, safer, and higher reliability.

Further object of the present invention is to provide a device for optimizing transmitting energy and transmitting position for an implantable element, which provides a solution for optimizing transmitting energy for all implantable elements.

According to those objects of the present invention mentioned above, there is provided a device for optimizing transmitting energy and transmitting position for an implantable electrical stimulator, which device comprises an external energy-transmitting module and an internal implantable module. The external energy-transmitting module is located outside an organism and comprises a first energy-transmitting antenna, a first wireless radio frequency interface circuit, an adjustable power control circuit, and an output control circuit. The first energy-transmitting antenna is used to perform wireless energy transmission. The first wireless radio frequency interface circuit is used to drive the first energy-transmitting antenna to emit energy and convert a sense signal received by the first energy-transmitting antenna into a first electronic signal. The adjustable power control circuit determines the optimum power control mode for transmitting energy based on the first electronic signal. The output control circuit outputs a corresponding output signal to the first wireless radio frequency interface circuit based on the optimum power control mode for transmitting energy, in order to drive the first energy-transmitting antenna to perform wireless energy transmission. The internal implantable module is implanted into the organism and comprises a second energy-transmitting antenna, a second wireless radio frequency interface circuit, a feedback modulation control circuit, and an electrical stimulating control circuit. The second energy-transmitting antenna receives the energy emitted by the first energy-transmitting antenna. The second wireless radio frequency interface circuit converts the received energy into a second electronic signal and then sends the second electronic signal to the feedback modulation control circuit. The feedback modulation control circuit determines based on the second electronic signal whether the electrical stimulating control circuit can be driven. If the determination result is yes, then the electrical stimulating control circuit is driven; or otherwise, a feedback signal is generated and sent out via the second energy-transmitting antenna and received by the first energy-transmitting antenna to form the sense signal.

As mentioned above, the device for optimizing transmitting energy and transmitting position for an implantable electrical stimulator according to the present invention utilizes a design of a wireless energy transmitting and positioning device with an external energy-feedback control, which can automatically detect an optimum energy-transmitting position through an external antenna performing an adjustable energy transmission method, and through a wireless-feedback control method to provide the optimum energy. As such, the purpose for treating sore nervous muscle and accelerating to recover injured organism is achieved.

DETAILED DESCRIPTION OF THE EMBODIMENTS

Several objects and advantages of the present invention will become clearer understood by the following detailed description of the embodiment with reference to accompanying drawings.

Figure 1:
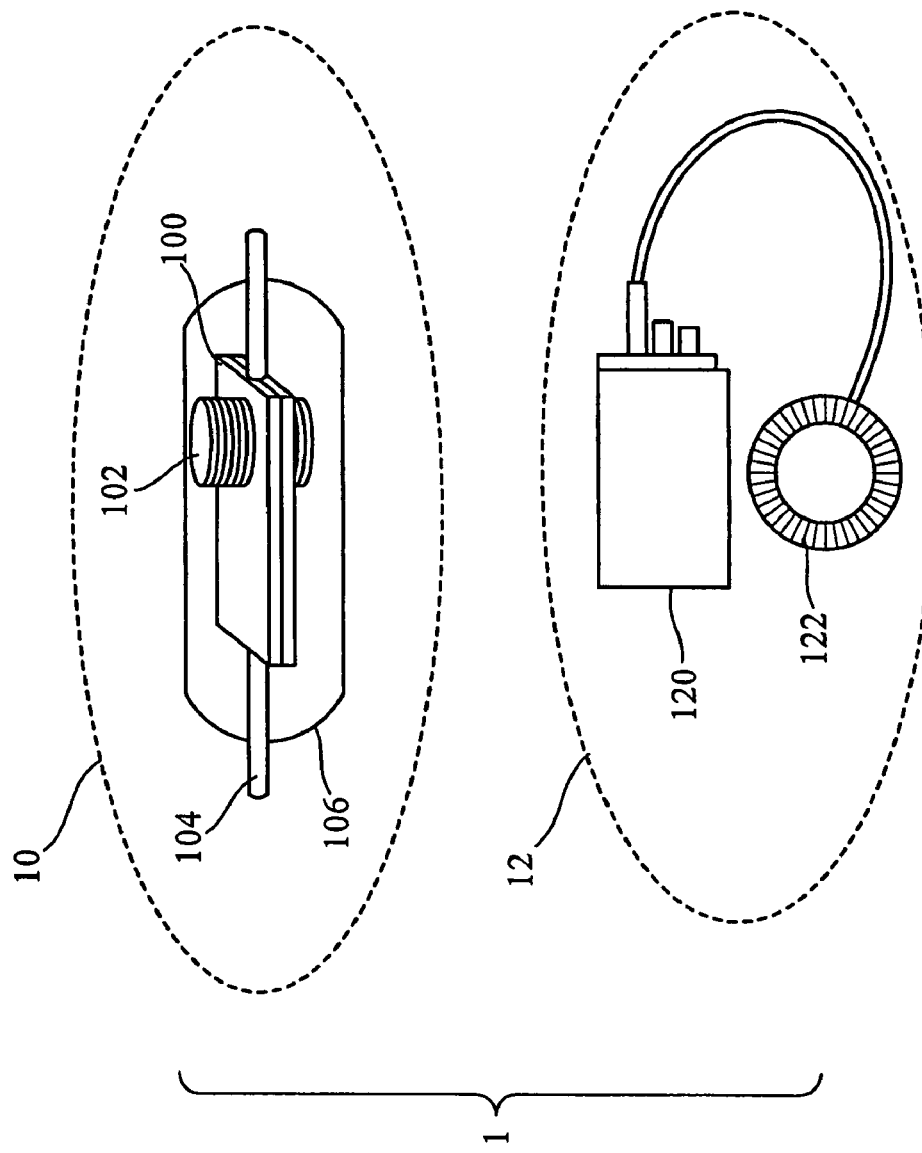
FIG. 1 is a schematic view of assembly of a conventional implantable electrical stimulating device.
Figure 2:
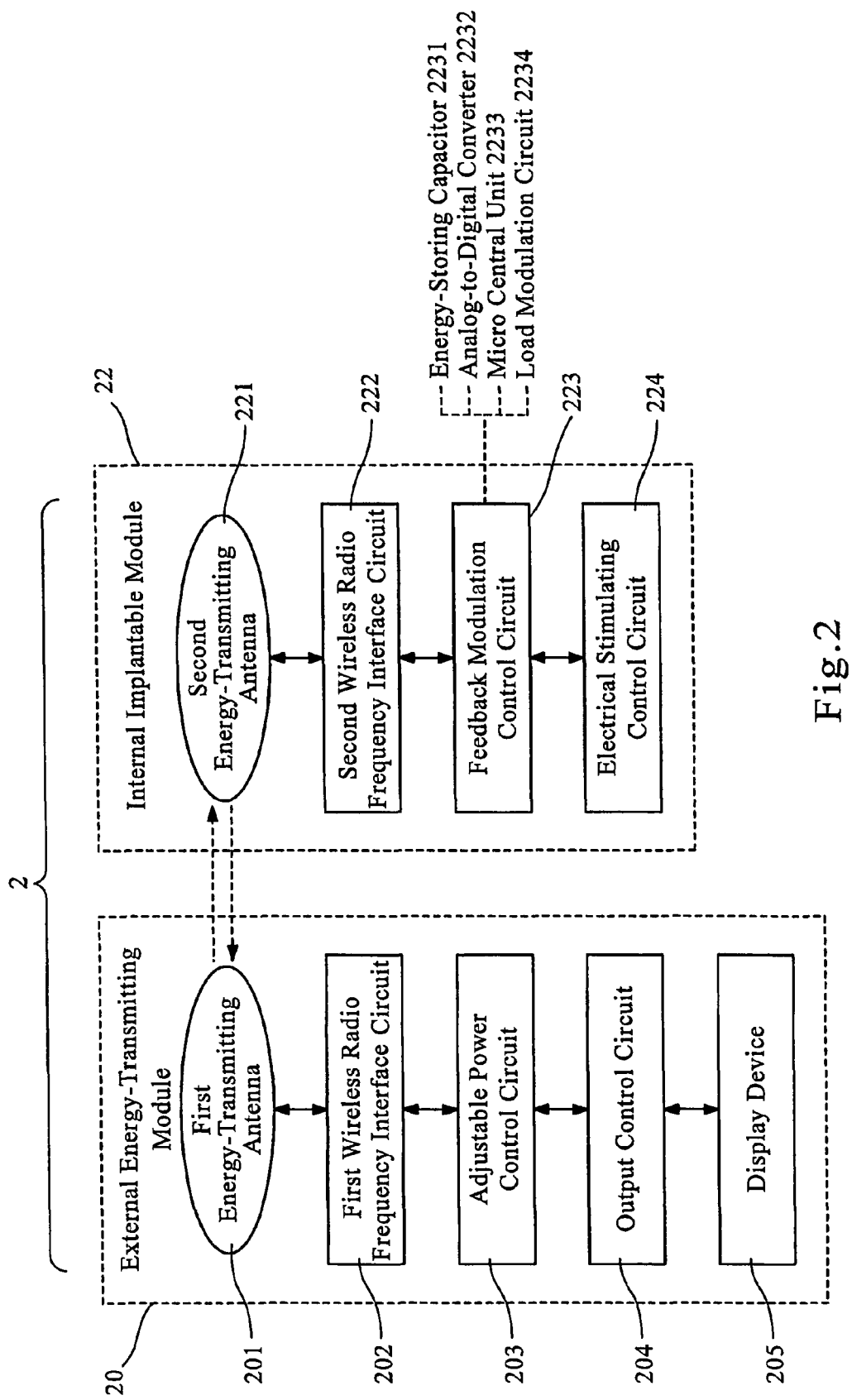
FIG. 2 is a functional block diagram of a device for optimizing transmitting energy and transmitting position for an implantable electrical stimulator according to the present invention.
Figure 3:
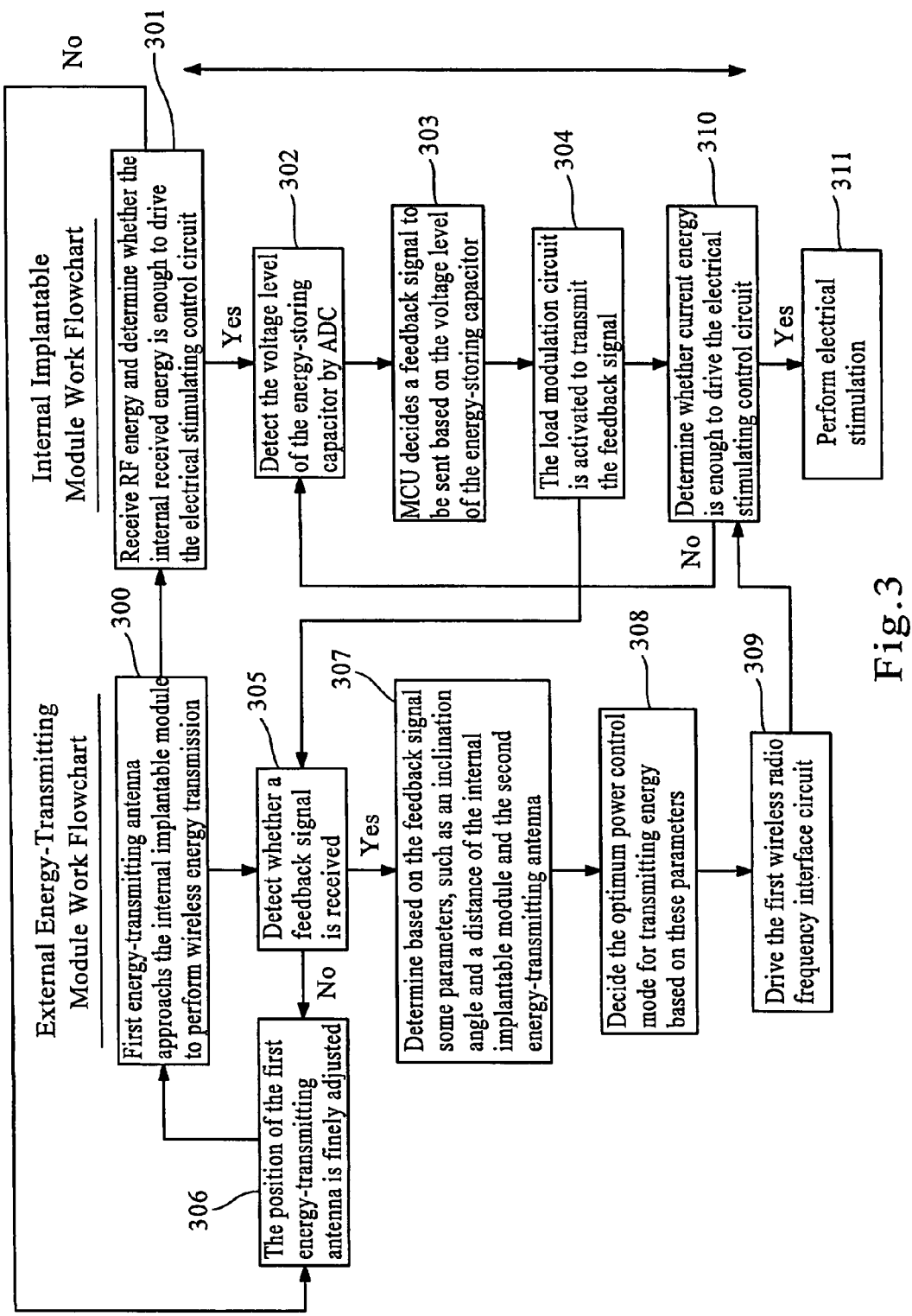
FIG. 3 is a flow chart of a device for optimizing transmitting energy and transmitting position for an implantable electrical stimulator according to the present invention.

FIG. 2 is a functional block diagram of an embodiment of a device for optimizing transmitting energy and transmitting position for an implantable electrical stimulator according to the present invention. FIG. 3 is a flow chart of the device for optimizing transmitting energy and transmitting position for an implantable electrical stimulator shown in FIG. 2. In this embodiment, the device for optimizing transmitting energy and transmitting position 2 for an implantable electrical stimulator comprises an external energy-transmitting module 20 and an internal implantable module 22. The external energy-transmitting module 20 is located outside an organism and the internal implantable module 22 is implanted into the organism. The external energy-transmitting module 20 is used to transmit power and data, and comprises a first energy-transmitting antenna 201, a first wireless radio frequency interface circuit 202, an adjustable power control circuit 203, an output control circuit 204, and a display device 205. The internal implantable module 22 comprises a second energy-transmitting antenna 221, a second wireless radio frequency interface circuit 222, a feedback modulation control circuit 223 and an electrical stimulating control circuit 224. Wherein the feedback modulation control circuit 223 further includes an energy-storing capacitor 2231, an ADC(Analog-to-Digital Converter) 2232, a MCU(Micro Central Unit) 2233, and a load modulation circuit 2234. The first energy-transmitting antenna 201 is used to perform wireless energy transmission. The first wireless radio frequency interface circuit 202 is used to drive the first energy-transmitting antenna 201 to emit energy and convert a sense signal received by the first energy-transmitting antenna 201 into a first electronic signal. The adjustable power control circuit 203 determines the optimum power control mode for transmitting energy based on the first electronic signal. The output control circuit 204 outputs a corresponding output signal to the first wireless radio frequency interface circuit 202 based on the optimum power control mode for transmitting energy, in order to drive the first energy-transmitting antenna 201 to perform wireless energy transmission. The second energy-transmitting antenna 221 receives the power and data in a form of energy emitted by the first energy-transmitting antenna 201. The second wireless radio frequency interface circuit 222 converts the received energy into a second electronic signal and then sends the second electronic signal to the feedback modulation control circuit 223. The MCU 2233 determines based on the second electronic signal whether the received energy is enough to drive the electrical stimulating control circuit 224. If the determination result is yes, then an electrical stimulation is performed; or otherwise, a feedback signal is generated based on the second electronic signal and sent out via the second energy-transmitting antenna 221 and received by the first energy-transmitting antenna 201 to form the sense signal. However, if the first energy-transmitting antenna 201 does not detect the feedback signal, then the position of the first energy-transmitting antenna 201 will be further adjusted until a feedback signal is detected.

The work principles and flowchart of the device for optimizing transmitting energy and transmitting position 2 for the abovementioned implantable electrical stimulator according to the present invention will be described in detail with reference to FIG. 2 and FIG. 3 in the following.

First, the external energy-transmitting module 20 is activated at step 300. The first energy-transmitting antenna 201 approaches the internal implantable module 22 to perform wireless energy transmission. Then at step 301, the wireless radio frequency energy is received by the second energy-transmitting antenna 221 of the internal implantable module 22 and converted by the second wireless radio frequency interface circuit 222 into the second electronic signal and sent to the feedback modulation control circuit 223. And, the MCU 2233 determines based on the second electronic signal whether the energy is enough to drive the electrical stimulating control circuit 224. If the determination result is yes, then the process proceeds to step 311, the electrical stimulating control circuit 224 is driven and an electrical stimulation is performed. Otherwise if the determination result is no, and then the process proceeds to step 302 and the ADC 2232 of the feedback modulation control circuit 223 detects the voltage level of the energy-storing capacitor 2231. And at step 303, the MCU 2233 of the feedback modulation control circuit 223 determines a feedback signal to be sent based on the voltage level of the energy-storing capacitor 2231. Thereafter, the load modulation circuit 2234 of the feedback modulation control circuit 223 is activated to transmit the feedback signal at step 304. Then the external energy-transmitting module 20 detects the feedback signal via the first energy-transmitting antenna 201 at step 305. If the first energy-transmitting antenna 201 does not detect the feedback signal, then the position of the first energy-transmitting antenna 201 is finely adjusted at step 306 and steps 300-305 is repeated until the feedback signal is detected by the first energy-transmitting antenna 201. When the first energy-transmitting antenna 201 has detected the feedback signal, the process proceeds to step 307. At step 307, the feedback signal is converted by the first wireless radio frequency interface circuit 202 into the first electronic signal and the first electronic signal is sent to the adjustable power control circuit 203. Based on the first electronic signal, the adjustable power control circuit 203 determines some parameters, such as the inclination angle and the distance of the second energy-transmitting antenna 221 and the first energy-transmitting antenna 201. At step 308, the adjustable power control circuit 203 determines the optimum power control mode for transmitting energy based on these parameters. Then at step 309, the output control circuit 204, e.g. a digital control circuit, outputs a corresponding output signal to the first wireless radio frequency interface circuit 202 based on the optimum power control mode for transmitting energy, in order to drive the first energy-transmitting antenna 201 to perform wireless energy transmission. Subsequently, steps 301 and 310 are performed, the second wireless radio frequency interface circuit 222 converts the received energy into a second electronic signal and determines based on the second electronic signal whether the received energy is enough to drive the electrical stimulating control circuit 224. If the determination result is yes, then the process proceeds to step 311, the electrical stimulating control circuit 224 is activated and an electrical stimulation is performed; or otherwise, steps 302 and 309 are repeated, until the electrical stimulating control circuit 224 can be activated. Moreover, the optimum power control mode for transmitting energy determined at step 308 determines the optimum orientation for transmitting energy and the optimum transmission energy for the first energy-transmitting antenna 201, and the display device 205, e.g. a liquid crystal display or light-emitting diode display, can display these results. The position of the first energy-transmitting antenna 201 can be finely adjusted by the user based on the displayed optimum orientation of the first energy-transmitting antenna 201.

As mentioned above, the device for optimizing transmitting energy and transmitting position for an implantable electrical stimulator according to the present invention can automatically detect an optimum energy-transmitting position through an external antenna performing an adjustable energy transmission method, and through a wireless-feedback control method to provide the optimum energy, such that the energy can be exactly and effectively transmitted to the implantable electrical stimulator via a wireless energy transmission method, thereby the implantable electrical stimulator can be used more comfortable, safer, and more convenient. In addition, the device for optimizing transmitting energy and transmitting position for an implantable electrical stimulator according to the present invention designs a two-step usage, such that the product can be used less complex and more convenient. The device for optimizing transmitting energy and transmitting position according to the_ present invention not only can be combined with an implantable electrical stimulator, but also can be combined with any implantable electronic element. Thus, the present invention provides a solution for optimizing transmitting energy for all implantable elements.

The above specific embodiments are only illustrative and does not intend limiting the scope of the present invention. And many variations can be introduced on these embodiments without departing from the spirit of the disclosure or from the scope of the appended claims.

What is claimed is:

1. A method for optimizing transmitting energy and transmitting position for an implantable electronic element, comprising:
    activating an external energy-transmitting module having an energy-transmitting antenna to drive said energy-transmitting antenna to emit energy;
    receiving said energy by an internal implantable module and determining by said internal implantable module based on said energy whether to drive said implantable electronic element or generate a feedback signal, wherein said implantable electronic element is driven if said energy is sufficient, and if said energy is insufficient, said feedback signal is generated;
    receiving said feedback signal by said external energy-transmitting module to determine an optimum power control mode for transmitting energy, a position of said energy-transmitting antenna is only adjusted when said implantable electronic element is not being driven; and
    transmitting energy based on said optimum power control mode for transmitting energy by said external energy-transmitting module;
    wherein said external energy-transmitting module receives said feedback signal and determines based on said feedback signal the relative position and the distance of said implantable electronic element and said energy-transmitting antenna to determine the optimum power control mode for transmitting energy, and an optimum orientation of said energy-transmitting antenna and its optimum transmission energy are determined accordingly, the position of said energy-transmitting antenna is adjusted based on the optimum orientation if necessary.

2. The method for optimizing transmitting energy and transmitting position for an implantable electronic element of claim 1, wherein further comprising adjusting the position of said energy-transmitting antenna when said feedback signal has not been received by said external energy-transmitting module, until said feedback signal is received.

3. The method for optimizing transmitting energy and transmitting position for an implantable electronic element of claim 2, wherein further comprising displaying the optimum orientation and the optimum transmission energy for said energy-transmitting antenna based on said optimum power control mode for transmitting energy.

4. The method for optimizing transmitting energy and transmitting position for an implantable electronic element of claim 2, wherein said implantable electronic element is an implantable electrical stimulator.

5. The method for optimizing transmitting energy and transmitting position for an implantable electronic element of claim 1, wherein further comprising displaying the optimum orientation and the optimum transmission energy for said energy-transmitting antenna based on said optimum power control mode for transmitting energy.

6. The method for optimizing transmitting energy and transmitting position for an implantable electronic element of claim 1, wherein said implantable electronic element is an implantable electrical stimulator.

7. A method for optimizing transmitting energy and transmitting position for an implantable electronic element, comprising:

activating an external energy-transmitting module by a first energy-transmitting antenna approaching an internal implantable module to perform wireless energy transmission;

receiving the wireless energy transmission by a second-energy-transmitting antenna of the internal implantable module;

converting the wireless energy transmission into a second electronic signal and sending the second electronic signal to a feedback modulation control circuit;

determining based on the second electronic signal whether the energy is enough to drive an electrical stimulation control circuit and when the energy is enough, then driving the electrical stimulation control circuit and performing electrical stimulation;

detecting the voltage level of an energy-storing capacitor if the energy is not enough to drive the electrical stimulation control circuit;

determining a feedback signal based on the voltage level of the energy-storing capacitor;

activating the feedback modulation control circuit to transmit the feedback signal;

detecting the feedback signal by the first energy-transmitting antenna wherein if no feedback signal is detected, then, the position of the first energy-transmitting antenna is adjusted until the feedback signal is detected by the first energy-transmitting antenna;

converting the feedback signal into a first electronic signal;

sending the first electronic signal to an adjustable power control circuit;

determining inclination angle and distance of the second energy-transmitting antenna and the first energy-transmitting antenna;

determining the optimum power control mode based on inclination angle and distance of the second energy-transmitting antenna and the first energy-transmitting antenna; and adjusting the position of the internal implantable module based on the optimum orientation.

* * * * *